United States Patent
Stuart

(10) Patent No.: US 10,682,785 B1
(45) Date of Patent: Jun. 16, 2020

(54) METHOD FOR PRODUCING A NEGATIVE CAST FOR A BRACE WITH CORRECTIVE FORCES TO CONTROL PLC DEFICIENCIES

(71) Applicant: William Stuart, Long Beach, CA (US)

(72) Inventor: William Stuart, Long Beach, CA (US)

( * ) Notice: Subject to any disclaimer, the term of this patent is extended or adjusted under 35 U.S.C. 154(b) by 618 days.

(21) Appl. No.: 15/413,719

(22) Filed: Jan. 24, 2017

(51) Int. Cl.
| | |
|---|---|
| *B28B 1/40* | (2006.01) |
| *A61F 5/01* | (2006.01) |
| *B28B 7/34* | (2006.01) |
| *A61F 2/50* | (2006.01) |
| *B29C 33/38* | (2006.01) |

(52) U.S. Cl.
CPC ............. *B28B 1/40* (2013.01); *A61F 5/0102* (2013.01); *A61F 5/0106* (2013.01); *A61F 5/0109* (2013.01); *B28B 7/344* (2013.01); *A61F 2002/5053* (2013.01); *A61F 2240/004* (2013.01); *B29C 2033/3871* (2013.01)

(58) Field of Classification Search
CPC ........ A61F 5/01; A61F 5/0102; A61F 5/0104; A61F 5/0106; A61F 5/0109; A61F 5/0111; A61F 5/0123; A61F 5/0127; A61F 2002/5053; A61F 2240/004; B28B 7/344; B28B 7/346; B29L 2031/7532; B29C 2033/3871
USPC .............................................. 264/223; 425/2
See application file for complete search history.

(56) References Cited

U.S. PATENT DOCUMENTS

| | | | |
|---|---|---|---|
| 4,217,893 A | * | 8/1980 | Payton ................. A61F 5/0585 602/12 |
| 4,493,316 A | | 1/1985 | Reed et al. |
| 4,506,661 A | | 3/1985 | Foster |
| 4,573,455 A | | 3/1986 | Hoy |
| 4,773,404 A | | 9/1988 | Townsend |
| 4,966,133 A | | 10/1990 | Kausek |
| 5,107,824 A | | 4/1992 | Rogers et al. |

(Continued)

FOREIGN PATENT DOCUMENTS

| | | |
|---|---|---|
| CA | 2145556 | 10/1995 |
| DE | 102009038517 | 6/2016 |

(Continued)

OTHER PUBLICATIONS

Ottobock, "Negative Plaster Casts—Test Orthosis Differences due to Brace Design," Published Jan. 22, 2017, Accessed Aug. 13, 2019. (Year: 2017).*

(Continued)

*Primary Examiner* — Seyed Masoud Malekzadeh
*Assistant Examiner* — Sonny V Nguyen
(74) *Attorney, Agent, or Firm* — Weiss & Moy, P.C.; Jeffrey D. Moy

(57) ABSTRACT

A casting method for a brace having corrective forces is disclosed. The foot is externally rotated during casting and corrective forces are applied at the lateral knee and anteromedial ankle. With the knee flexed at between about 70° to 90°, the cast is fully extended, which places the knee in a position which will reduce the pressures on the medial knee. This is the position desired during the casting process with the knee flexed and then held while extending the knee. The result is control of the posterior lateral rotation, therefore controlling the posterior subluxation of the tibial plateau to achieve the motion and alignment that the screw home motion produces.

14 Claims, 3 Drawing Sheets

(56) References Cited

U.S. PATENT DOCUMENTS

| | | | |
|---|---|---|---|
| 6,387,066 B1 | 5/2002 | Whiteside | |
| 6,565,523 B1 | 5/2003 | Gabourie | |
| 7,097,799 B1* | 8/2006 | Burton | A61F 2/5046 |
| | | | 264/220 |
| 9,220,624 B2* | 12/2015 | Jansson | A61F 5/0125 |
| 2004/0054311 A1 | 3/2004 | Sterling | |
| 2005/0192523 A1 | 9/2005 | Knecht et al. | |
| 2012/0238928 A1* | 9/2012 | Buethorn | A61F 5/0111 |
| | | | 602/27 |
| 2013/0041289 A1 | 2/2013 | Sena et al. | |
| 2014/0221891 A1 | 8/2014 | Sreeramagirl et al. | |
| 2015/0051527 A1 | 2/2015 | Potter et al. | |
| 2016/0051389 A1 | 2/2016 | Seligman | |
| 2016/0151188 A1 | 6/2016 | Romo | |
| 2017/0252200 A1* | 9/2017 | Taylor | A61F 5/34 |

FOREIGN PATENT DOCUMENTS

| | | |
|---|---|---|
| EP | 2215993 | 3/2014 |
| WO | 1993022992 | 5/1992 |

OTHER PUBLICATIONS

Ottobock, "Fabrication of a knee-ankle-foot orthosis using thermoplastic technology," Published Jun. 13, 2014, Accessed Aug. 13, 2019. (Year: 2014).*

Richie Brace, "Richie Brace Treatment Guide: Tips for Evaluation, Casting, Prescription, Modifications, and Troubleshooting", Published Jan. 19, 2015, Accessed Aug. 13, 2019. (Year: 2016).*

Genu Recurvatum: Identification of Three Distinct Mechanical Profiles Fish et al http://www.oandp.org/jpo/library/1998_02_026.asp.

The Effect of Injury to the Posterolateral Structures of the Knee on Force in a Posterior Cruciate Ligament Graft A Biomechanical Study Laprade et al. http://journals.sagepub.com/doi/pdf/10.1177/03635465020300021501.

Current concepts review: comprehensive physical examination for instability of the knee. Taos Orthopaedic Institute Research Foundation, Jan. 24, 2008 https://www.ncbi.nlm.nih.gov/pubmed/18219052.

The Biomechanics of Toe-Out Gait Modification in People With and Without Knee Osteoarthritis Takacs et al. http://prgmobileapps.com/AppUpdates/ors/Abstracts/abs1233.html.

Relationship between foot function and medial knee joint loading in people with medial compartment knee osteoarthritis Levinger et al. Journal of Foot and Ankle Research https://jfootankleres.biomedcentral.com/articles/10.1186/1757-1146-6-33.

Correction of Hyperextension Gait Abnormalities: Preoperative and Postoperative Techniques http://clinicalgate.com/correction-of-hyperextension-gait-abnormalities-preoperative-and-postoperative-techniques/.

Secondary motions of the knee during weight bearing and non-weight bearing activities Chris O. Dyrby, Thomas P. Andriacchi http://onlinelibrary.wiley.com/doi/10.1016/j.orthres.2003.11.003/epdf.

Shock Doctor Ultra Knee Support With Hinges http://www.eastbay.com/product/model:203778/shock-doctor-ultra-knee-support-with-hinges/black/&SID=7726.

Lenox Hill Swedish Knee Cage https://www.amazon.com/Lenox-Hill-Swedish-Knee-Cage/dp/B00N3ITX7M?th=1.

* cited by examiner

METHOD FOR PRODUCING A NEGATIVE CAST FOR A BRACE WITH CORRECTIVE FORCES TO CONTROL PLC DEFICIENCIES

FIELD OF THE INVENTION

The present invention generally relates to orthoses and more specifically, a method for producing a negative cast for a brace with corrective forces to control PLC deficiencies.

BACKGROUND OF THE INVENTION

Orthoses are external supports (braces) for the body, which are custom fitted and/or custom fabricated for the specific needs of the patient. The typical process for creating a brace for a patient includes patient assessment, formulation of a treatment plan for the patient, implementation of the treatment plan, follow-up, and practice management.

The procedures traditionally used to produce a knee orthosis (KO) only involve the use of measurements or creating a negative cast (which is wrapped on the patient). When the brace is produced from a cast, some manufacturers instruct practitioners to position the patient's knee in full extension without corrective forces applied during the procedure. The manufacturer then modifies the positive cast (by filling the negative cast with plaster—the hardened plaster results in the negative cast) to provide the corrective forces. The prior art has soft anterior shells, very narrow hard shells, or larger shells made from non-corrective casts, and do not extend proximally over the tibial condyles, not having corrective forces applied during casting or measuring.

The prior art procedures traditionally used to produce a knee ankle foot orthosis (KAFO) involve different procedures to cast for the KAFO, which may include tri-planar design in the foot and ankle, but only bi-planar design at the knee. Those procedures control knee movement in the coronal (frontal—for viewing varus and valgus of the knee) and saggital (side—for viewing flexion and extension of the knee) planes only. Those traditional procedures do not address deformities of the knee in the transverse plane (rotation—internal and external movement), which are addressed by the invention disclosed herein. When patients have posterolateral corner (PLC) injuries or deficits, all three planes are involved. Until now the knee has only been supported in two planes simultaneously. To achieve optimal results, the knee must be controlled in all three planes.

Rotating the foot to try and produce external rotation only slightly effects the knee. It is also difficult or not possible to achieve neutral or external foot rotation with some patients with moderate to severe neuroskeletal deficits or deformities. This invention is unique in the process of achieving the tri-planar support desired to produce an orthosis that controls posterolateral movement of the knee. Traditionally, the procedures to produce a negative cast for a KAFO involves the cast being applied to the patient, then corrective three point pressures are applied to the proximal medial thigh (directing pressures laterally), to the lateral knee or proximal lateral calf (to direct pressures medially), and a medial pressure is applied at the distal calf (directing pressure laterally). These pressures are applied with the patient's knee straight or slightly flexed with the foot having no correction or correction made after the upper section was cast. This traditional method does not produce the rotational alignment required to achieve the maximum benefit to the patient. Even a cast taken with the external rotary deficiency (ERD) corrections to the foot does not affect the rotation of the knee adequately. The present invention disclosed herein is unique in the process of achieving the tri-planar support desired to produce an orthosis that controls posterolateral movement of the knee and restore the screw home motion of a normal knee.

SUMMARY

In accordance with one embodiment of the present invention, a method for creating a negative cast of a human leg is disclosed. The method comprises the steps of: initially positioning the leg with a knee bent at an angle between approximately 15° and 50°; wrapping casting material around the leg while the knee is positioned at the angle between approximately 15° and 50°; bending the knee in a position of flexion at an angle between approximately 70° and 90°; applying corrective forces to the knee while it is positioned at the angle between approximately 70° and 90°; extending the knee while continuing to apply the corrective forces to the knee; allowing the casting material to dry; and removing the casting material from the leg.

In accordance with another embodiment of the present invention, a method for creating a negative cast of a human leg is disclosed. The method comprises the steps of: initially positioning the leg with a knee bent at an angle of approximately 45°; wrapping casting material around the leg while the knee is positioned at the angle of 45°; bending the knee in a position of flexion at an angle of approximately 85°; applying corrective forces to the knee while it is positioned at the angle of 85°; extending the knee while continuing to apply the corrective forces to the knee; allowing the casting material to dry; and removing the casting material from the leg In accordance with another embodiment of the present invention, a method for creating a negative cast of a human leg is disclosed. The method comprises the steps of: initially positioning the leg with a knee bent at an angle of approximately 45°; wrapping casting material around the leg while the knee is positioned at the angle of 45°; bending the knee in a position of flexion at an angle of approximately 85°; applying corrective forces to the knee while it is positioned at the angle of 85°, wherein the step of applying corrective forces to the knee comprises the steps of: applying valgus directed pressure to the knee and ankle; and applying external tibial rotation of a foot and an ankle of the leg; fully extending the knee while continuing to apply the corrective forces to the knee; allowing the casting material to dry; and removing the casting material from the leg.

BRIEF DESCRIPTION OF THE DRAWINGS

The present application is further detailed with respect to the following drawings. These figures are not intended to limit the scope of the present application, but rather, illustrate certain attributes thereof.

DETAILED DESCRIPTION OF THE INVENTION

Figure 1:
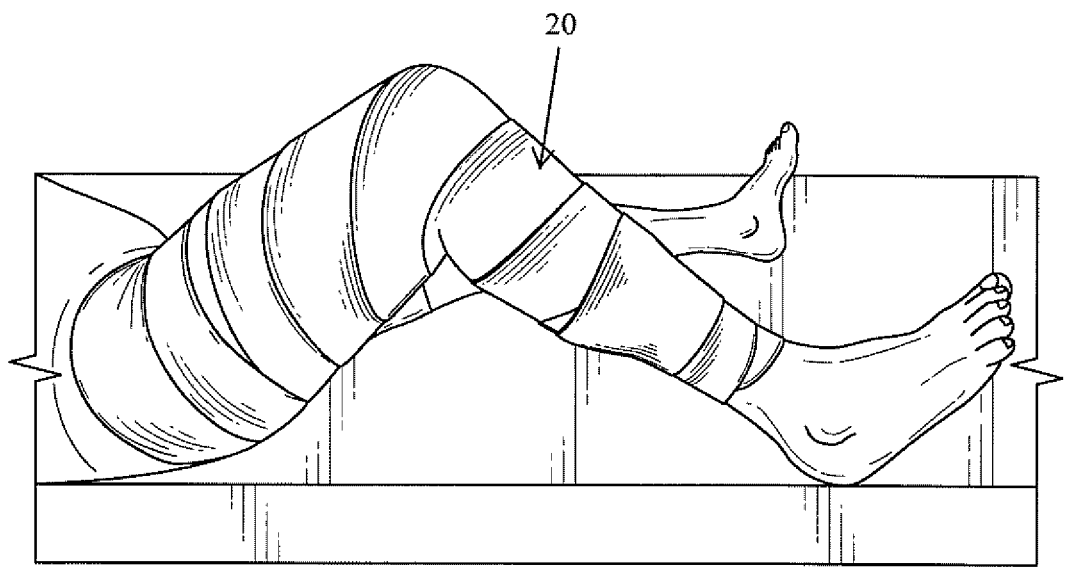
FIG. 1 is a side view of the step of applying plaster material to a patient's right leg wherein the patient's right leg bent at about a 45° angle, in accordance with one or more aspects of the present invention.

The description set forth below in connection with the appended drawings is intended as a description of presently preferred embodiments of the disclosure and is not intended to represent the only forms in which the present disclosure may be constructed and/or utilized. The description sets forth the functions and the sequence of steps for constructing and operating the disclosure in connection with the illustrated embodiments. It is to be understood, however, that the same or equivalent functions and sequences may be accomplished by different embodiments that are also intended to be encompassed within the spirit and scope of this disclosure.

FIGS. 1-5, together, disclose the method for providing a negative cast to be used to fabricate the orthosis for a patient suffering from posterolateral corner deficit. The present invention provides innovative casting techniques applied during the process of producing a negative corrective cast which is an important component of the fabrication process for the KO or KAFO brace. The resulting cast is unique in the procedures used to position the patient's leg and the corrective forces applied. This results in a cast and orthosis which is going to prevent the knee from externally rotating and control genu recurvatum and genu varum by performing the procedures in the reverse pivot shift test. The disclosed method discloses steps for controlling tri-planar movement of the posterolateral corner of the knee during casting.

This invention is unique in the process of achieving an orthosis which controls recurvatum, rotation and varum of the knee by providing the tri-planar support. The traditional methods in this art have not been used to cast and produce an orthosis in this manner to achieve the resulting reduction of posterolateral movement of the knee and unloading the medial compartment, which also reduces pain and progression of deterioration of the medial knee capsule. In order to achieve optimal results, the knee must be controlled in all three planes: coronal, saggital, and transverse.

Disclosed herein is a method of designing a brace used to provide support and control of the knee movement, specifically external rotation, recurvatum and *varus*, by restoring the natural screw home motion. It will also prevent the posterior subluxation of the lateral tibial plateau and genu recurvatum due to deficiencies of the posterolateral corner (PLC) of the knee. Using the present method to produce the orthosis (KO or KAFO) will prove to superiorally unload the medial compartment, which will prevent deterioration of the knee joint by realigning the knee in a more natural position. This will decrease pain and improve the quality of life for many people.

In a normal knee, a movement known as screw-home motion occurs. This is passive femoral rollback (posterior displacement of the femur with respect to the tibia), which occurs as the knee flexes from full extension. In patients with deficiencies of the PLC, the screw-home motion is simulated by the casting technique disclosed herein to obtain the desired result. During the casting process the knee is flexed and then held in the corrected position while extending the knee and maximally externally rotating the foot. This controls the rotation and posterior subluxation of the tibial plateau. This specific design technique has not been previously used by practitioners to control this type of deficiency in the knee.

The present invention addresses an aspect of the field of art that has not previously been addressed properly. The tri-planar motions of the foot and ankle have been previously recognized and resolutions have been discovered. A combination of these tri-planar motions has been identified as external rotary deformity (ERD). However, the rotational components of the knee have not been resolved until now. In previous research on genu recurvatum, the foot and ankle have a tone-induced equinovarus positioning, which means that when the forefoot is in adduction, supination, and plantarflexed position and the calcaneous is sustained in a position of varus and dorsiflexion, the anterior-lateral lever function has been decreased. This causes the foot to become rigid and prevents the normal pronation moment from occurring during initial stance. This external torque is immediately transferred to the talocrural joint as well as proximally through the tibia to the knee in a closed kinetic chain (when the foot is in contact with the ground). As the talocrural joint externally rotates, the knee joint is now displaced in a posterior-lateral direction with external rotation of the knee. Posterior deviation (hyperextension) and genu varum (outward bowing of the knee) is most pronounced around mid-stance.

Many individuals suffer from deficiencies of the posterolateral corner (PLC) of the knee. PLC deficiencies usually occur from musculoskeletal diseases or disorders. This deformity of the PLC may also be caused by ligament injury or stress due to imbalance of muscles on the knee caused by musculoskeletal condition. Another cause may also occur due to the failure of the posterior collateral ligament grafts which increase the forces on the posterior cruciate ligament and create a varus moment coupled with posterior drawer force and external rotation torque. Another cause of PLC may be traumatic injury.

To identify a person who has a PLC deformity, the practitioner must perform a visual exam as well as clinical exam such as the posterolateral drawer test, external rotation recurvatum test, adduction stress test at 30° of knee flexion, dial test at 30° and 90°, and the reverse pivot shift test. These tests are considered to be the most reliable tests for determining posterolateral injury. The techniques used in performing the reverse pivot shift test proved to be beneficial as a technique incorporated into the casting method presented herein.

To perform the reverse pivot shift test, the patient is placed in the supine position with the knee flexed to about 85° and the tibia in maximum external rotation. The practitioner places a hand on the proximal lateral tibia, applying valgus directed pressure to the knee and ankle while maintaining external tibial rotation from the foot and ankle. An axial load is also applied as the examiner's other hand is placed just distal to the first on the anteromedial tibia at the mid-shaft so as to gain full contact of the distal leg. The examiner then begins to extend the knee while maintaining external rotation, axial load, and valgus force on the tibia. In a patient with posterolateral rotary instability, the lateral tibial plateau will be posterially subluxed at the onset of the test. As the knee is passively extended by the practitioner, the lateral tibial plateau will reduce with a palpable shift or jerk when the knee is extended to about 30°. This occurs as the pull of the iliotibial band changes from a flexion vector to an extension vector, thereby reducing the rotary subluxation through its pull on the Gerdy tubercle (where the iliotibial band attaches to the tibia).

By externally rotating the foot it will reduce external knee adduction moment (KAM). KAM is a measurement of the torque (a tendency of the force to rotate an object about an axis) that adducts the knee during the stance phase of gait. It has been previously found that externally rotating the foot and having the individual walk with an increased toe-out gait reduced medial loading of the knee and lead to a significantly decreased external KAM. The greater the KAM the greater the medial compartment varus alignment occurs. Peak KAM has been implicated in the progression of medial compartment OA (osteoarthritis). Although this has been important information regarding the reduction of medial knee joint pressures and pain, it has not been incorporated into traditional methods of casting of orthoses to result in controlling genu varum and external knee adduction moment. The present method herein used with the reverse pivot shift test process goes beyond prior casting methods and contributes to fabrication of orthoses that more effectively control the movement of the knee to a more natural alignment, thereby unloading the medial compartment of the knee, reducing pressures and pain.

When a cast is taken for a knee brace, traditionally the corrective forces are only applied in two planes without any attention to the position of the foot. In method of the present invention, the casting process for the negative cast of a KAFO and a KO begins with the patient in a supine position. FIG. 1 shows the patient in a supine position with his right knee bent in an angle of approximately 45°. The knee may be bent in an angle of between about 15°-50°. Prior to casting, a stocking may be wrapped about the patient's leg. Casting material 20 is then wrapped around the patient's leg, over the stocking. For a KO, casting material 20 is preferably wrapped around the patient's leg from the proximal thigh down to the distal calf just above the ankle (see FIGS. 1-3). For a KAFO, the casting material 20 will also cover the patient's foot (see FIGS. 4-5). The casting material 20 may comprise gauze combined with plaster of Paris which is a gypsum plaster consisting of a fine white powder (calcium sulfate hemihydrate) that hardens when moistened and allowed to dry, may be used. It should be clearly understood that substantial benefit may also be obtained from the use of other suitable casting materials 20. A cut strip may be inserted between the stocking and the casting material 20, which is used to protect the patient's leg when the cast is cut off.

Figure 2:
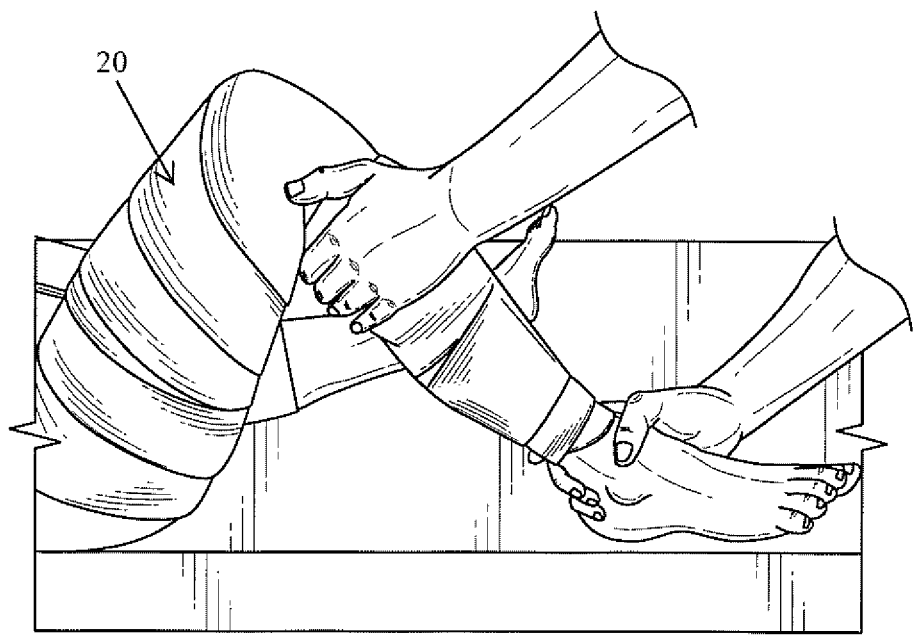
FIG. 2 is side view of the step of applying corrective forces to the patient's right leg wherein the patient's right leg is bent at about a 85° angle, in accordance with one or more aspects of the present invention.
Figure 3:
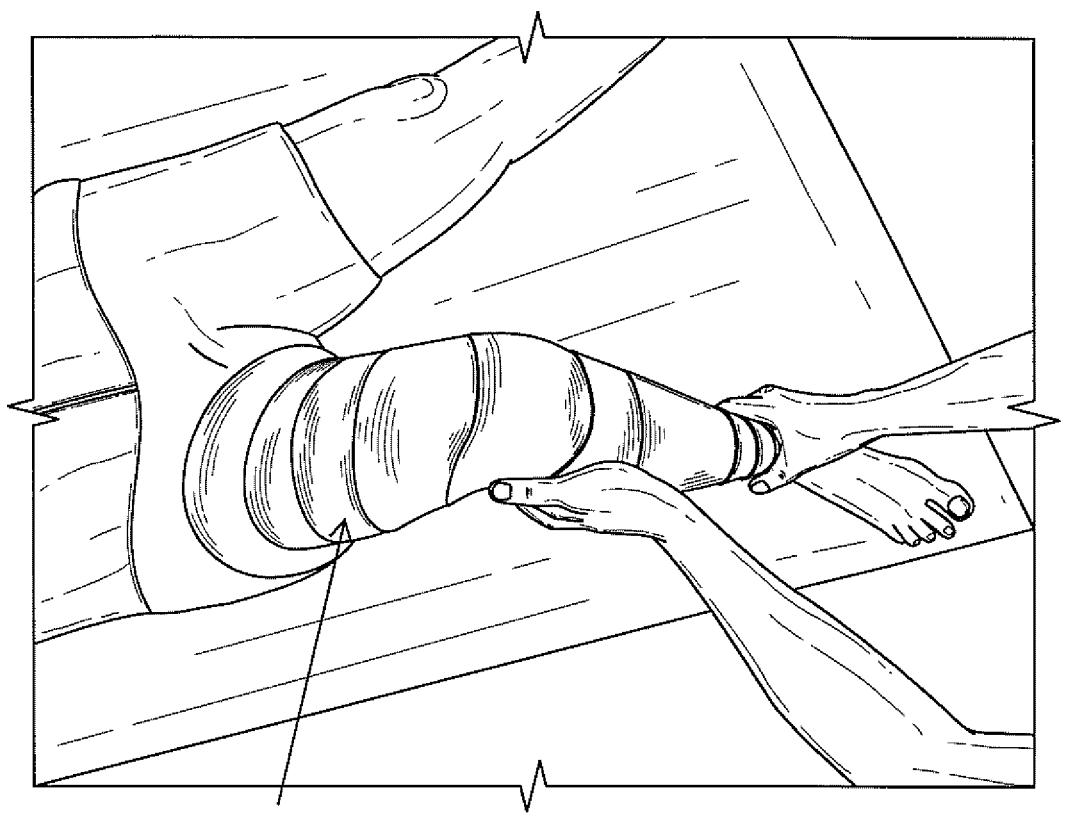
FIG. 3 is top view of the step of FIG. 2.

Referring to FIGS. 2-3, after the casting material 20 is applied to the patient's leg, the practitioner (or other health care provider) will bend the patient's knee in a position of flexion between about 70°-90° degrees, with a preferred angle at 85. The practitioner will then apply corrective forces to the patient's knee. Specifically, the practitioner will apply valgus directed pressure by placing one hand on the patient's lateral knee and pushing/directing pressure medially while the practitioner's other hand is simultaneously placed on the patient's anteromedial ankle and talus and pushing/directing pressure laterally while also externally rotating (external tibial rotation) the patient's foot. This hand positioning gives the practitioner leverage to apply laterally directed valgus forces to the lower limb while maximally externally rotating the foot simultaneously.

Figure 4:
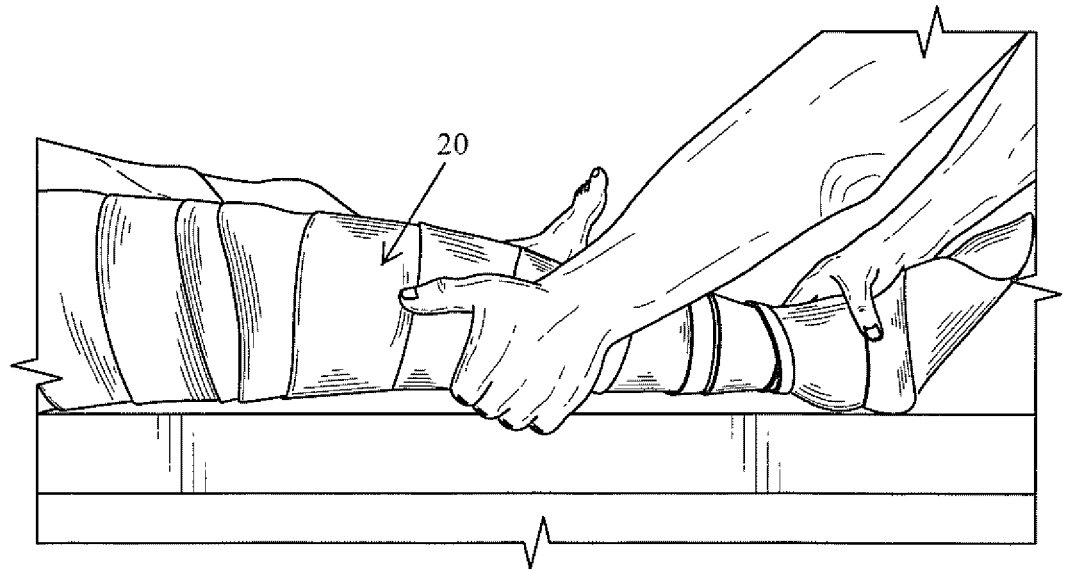
FIG. 4 is a side view of the step of fully extending the patient's right leg wherein corrective forces are still applied, in accordance with one or more aspects of the present invention.
Figure 5:
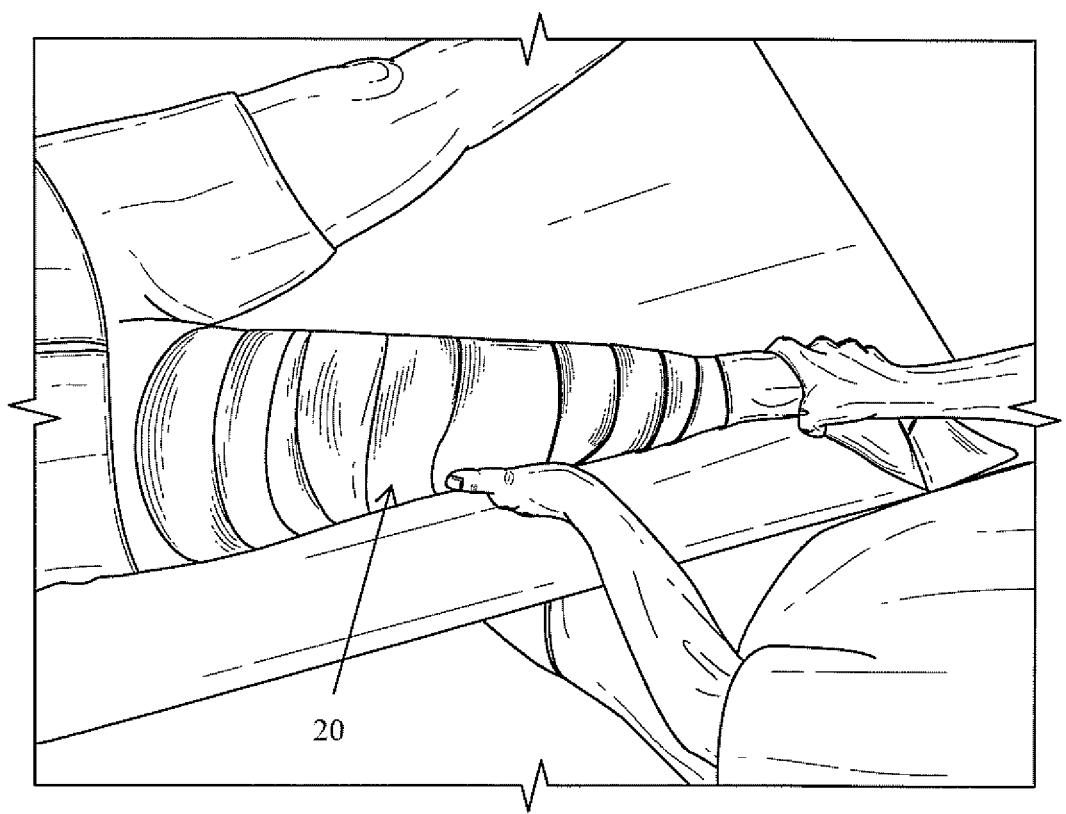
FIG. 5 is a top view of the step of FIG. 4.

Referring to FIGS. 4-5, while maintaining this corrected position; i.e. while maintaining valgus pressure and external rotation of the foot, the leg is then fully extended. It should also be understood that substantial benefit may also be derived if the leg is extended to an angle that is 5° short of full extension. If the patient requires a KAFO, the negative casting process involves the cast of the foot being attached and overlapping the proximal portion. If the foot requires correction as with ERD (external rotary deficiency), the cast is applied, maintaining corrective pressure and overlapping the proximal portion. The negative cast is then allowed to dry and removed by cutting it along the cut strip. The negative cast is then used to produce a positive cast and fabricate the orthosis. The positive cast is produced by filling the negative cast with plaster of Paris or other foam material. The positive cast therefore mimics the shape of the patient's leg and the brace is made to fit about the positive cast. The result is that the brace is specifically fitted for that patient's leg and the brace provides the corrective forces needed for that patient.

This new method of producing an orthosis would benefit the patient who has been diagnosed by a physician as having a posterolateral corner deficiency. It may be combined with posterior cruciate tear. A posterolateral corner deficiency is a condition which occurs when the primary structures of the posterior knee fail to resist the opening of the tibiofemoral compartment, posterior subluxation of the lateral tibial plateau with tibial rotation, knee hyperextension and varus recurvatum.

With the method disclosed herein, the foot is externally rotated during casting and forces are applied at the lateral knee and anteromedial ankle. With the knee flexed at between about 70° to 90°, the cast is fully extended, which places the knee in a position which will reduce the pressures on the medial knee. This is the position desired during the casting process with the knee flexed and then held while extending the knee. The result is control of the posterior lateral rotation, therefore controlling the posterior subluxation of the tibial plateau to achieve the motion and alignment that the screw home motion produces.

The foregoing description is illustrative of particular embodiments of the application, but is not meant to be limitation upon the practice thereof. While embodiments of the disclosure have been described in terms of various specific embodiments, those skilled in the art will recognize that the embodiments of the disclosure may be practiced with modifications within the spirit and scope of the claims.

I claim:

1. A method for creating a negative cast of a human leg comprising the steps of:
   initially positioning the leg with a knee bent at an angle between approximately 15° and 50°;
   wrapping casting material around the leg while the knee is positioned at the angle between approximately 15° and 50°, wherein the casting material is wrapped from a proximal thigh area of the leg to a distal calf area above an ankle of the leg;
   bending the knee in a position of flexion at an angle between approximately 70° and 90° after the casting material is wrapped from the proximal thigh area of the leg to the distal calf area above the ankle of the leg;
   applying corrective forces to the knee while the knee is positioned at the angle between approximately 70° and 90° wherein applying corrective forces to the knee comprises the steps of:
   applying valgus directed pressure to the knee; and
   externally rotating a foot of the leg;
   extending the knee while continuing to apply the corrective forces to the knee;
   allowing the casting material to dry; and
   removing the casting material from the leg.

2. The method of claim 1 wherein the knee is positioned at an angle of 45° when the casting material is wrapped around the leg.

3. The method of claim 1 wherein the casting material is further wrapped around a foot of the leg.

4. The method claim 1 wherein the knee is bent in the position of flexion of 85° while the casting material is wrapped around the leg.

5. The method of claim 1 wherein the step of applying valgus directed pressure to the knee comprises the steps of:
    placing one hand on a lateral knee area of the leg and directing pressure medially; and
    placing another hand on an anteromedial ankle and talus of the leg and directing pressure laterally.

6. The method of claim 1 wherein the knee is extended fully.

7. The method of claim 1 wherein the knee is extended to an angle that is 5° short of full extension.

8. A method for creating a negative cast of a human leg comprising the steps of:
    initially positioning the leg with a knee bent at an angle of approximately 45°;
    wrapping casting material around the leg while the knee is positioned at the angle of approximately 45°, wherein the casting material is wrapped from a proximal thigh area of the leg to a distal calf area above an ankle of the leg and wherein the negative cast is used for creation of a knee orthosis;
    bending the knee in a position of flexion at an angle of approximately 85° after wrapping the casting material from the proximal thigh area of the leg to the distal calf area above the ankle of the leg;
    applying corrective forces to the knee while the knee is positioned at the angle of approximately 85°, wherein the step of applying corrective forces to the knee comprises the steps of:
        applying valgus directed pressure to the knee; and
        applying external tibial rotation of a foot and the ankle of the leg;
    extending the knee while continuing to apply the corrective forces to the knee;
    allowing the casting material to dry; and
    removing the casting material from the leg.

9. The method of claim 8 wherein the casting material is further wrapped around a foot of the leg and wherein the negative cast is used for creation of a knee ankle foot orthosis.

10. The method of claim 8 wherein the step of applying valgus directed pressure to the knee comprises the steps of:
    placing one hand on a proximal lateral tibia of the leg and directing pressure medially; and
    placing another hand on an anteromedial ankle and talus of the leg and directing pressure laterally.

11. The method of claim 8 wherein the knee is extended fully.

12. The method of claim 8 wherein the knee is extended to an angle that is 5° short of full extension.

13. A method for creating a negative cast of a human leg comprising the steps of:
    initially positioning the leg with a knee bent at an angle of approximately 45°;
    wrapping casting material around the leg while the knee is positioned at the angle of approximately 45°, wherein the casting material is wrapped from a proximal thigh area of the leg to a distal calf area above an ankle of the leg;
    bending the knee in a position of flexion at an angle of approximately 85° after wrapping the casting material from the proximal thigh area of the leg to the distal calf area above the ankle of the leg;
    applying corrective forces to the knee while the knee is positioned at the angle of approximately 85°, wherein the step of applying corrective forces to the knee comprises the steps of:
        applying valgus directed pressure to the knee; and
        applying external tibial rotation of a foot and the ankle of the leg;
    fully extending the knee while continuing to apply the corrective forces to the knee;
    allowing the casting material to dry; and
    removing the casting material from the leg.

14. The method of claim 13 wherein the step of applying valgus directed pressure comprises the steps of:
    placing one hand on a proximal lateral tibia of the leg and directing pressure medially; and
    placing another hand on an anteromedial ankle and talus of the leg and directing pressure laterally.

* * * * *